US00PP17058P2

(12) United States Plant Patent
Arts

(10) Patent No.: US PP17,058 P2
(45) Date of Patent: Aug. 22, 2006

(54) ***KALANCHOE* PLANT NAMED 'ZION'**

(50) Latin Name: *Kalanchoe blossfeldiana*
Varietal Denomination: Zion

(75) Inventor: Niels Arts, Aalsmeer (NL)

(73) Assignee: AB Breeding, DeKwakel (NL)

( * ) Notice: Subject to any disclaimer, the term of this patent is extended or adjusted under 35 U.S.C. 154(b) by 0 days.

(21) Appl. No.: 11/146,228

(22) Filed: Jun. 6, 2005

(51) Int. Cl.
*A01H 5/00* (2006.01)

(52) U.S. Cl. ..... Plt./340
(58) Field of Classification Search ..... Plt./340
See application file for complete search history.

(56) References Cited

PUBLICATIONS

UPOV ROM GITIM Computer Database, GTI Jouve Retrieval Software 2005/04 Citation for 'Zion'.*
http://www.ma.ws–pro.com/Kalanchoe.html.*

* cited by examiner

*Primary Examiner*—Kent Bell
*Assistant Examiner*—W. C. Haas
(74) *Attorney, Agent, or Firm*—C. A. Whealy

(57) ABSTRACT

A new and distinct cultivar of *Kalanchoe* plant named 'Zion', characterized by its dark orange-colored flowers; upright and uniform plant habit; freely branching growth habit; early and freely flowering habit; and excellent post-production longevity.

1 Drawing Sheet

Botanical designation: *Kalanchoe blossfeldiana.*
Cultivar denomination: 'Zion'.

BACKGROUND OF THE INVENTION

The present invention relates to a new and distinct cultivar of *Kalanchoe* plant, botanically known as *Kalanchoe blossfeldiana,* and hereinafter referred to by the name 'Zion'.

The new *Kalanchoe* is a product of a planned breeding program conducted by the Inventor in Aalsmeer and Middelburg, The Netherlands. The objective of the breeding program was to create new compact and freely-branching *Kalanchoe* cultivars with attractive foliage and flower coloration.

The new *Kalanchoe* originated from a cross made by the Inventor in October, 2000 in Aalsmeer, The Netherlands of a proprietary selection of *Kalanchoe blossfeldiana* identified as code number 93104-15, not patented, as the female, or seed, parent with a proprietary selection of *Kalanchoe blossfeldiana* identified as code number 95018, not patented, as the male, or pollen, parent. The cultivar Zion was discovered and selected by the Inventor as a flowering plant within the progeny of the stated cross in a controlled environment in Middelburg, The Netherlands in August, 2001.

Asexual reproduction of the new *Kalanchoe* by terminal vegetative cuttings taken at Aalsmeer, The Netherlands, since August, 2001 has shown that the unique features of this new *Kalanchoe* are stable and reproduced true to type in successive generations.

BRIEF SUMMARY OF THE INVENTION

The cultivar Zion has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Zion'. These characteristics in combination distinguish 'Zion' as a new and distinct cultivar:

1. Dark orange-colored flowers.
2. Upright and uniform plant habit.
3. Freely branching growth habit.
4. Early and freely flowering habit.
5. Excellent postproduction longevity.

Plants of the new *Kalanchoe* can be compared to plants of the parent selections. In side-by-side comparisons conducted by the Inventor in De Kwakel, The Netherlands, plants of the new *Kalanchoe* differed from plants of the parent selections primarily in flower color as plants of the female parent selection had yellow-colored flowers and plants of the male parent selection had darker orange-colored flowers. In addition, plants of the new *Kalanchoe* had stronger roots than plants of the male parent selection.

Plants of the new *Kalanchoe* can also be compared to plants of the *Kalanchoe* cultivar Nadia, not patented. In side-by-side comparisons conducted by the Inventor in De Kwakel, The Netherlands, plants of the new *Kalanchoe* differed from plants of the cultivar Nadia in the following characteristics:

1. Plants of the new *Kalanchoe* were more compact than plants of the cultivar Nadia.
2. Plants of the new *Kalanchoe* were more freely branching than plants of the cultivar Nadia.
3. Plants of the new *Kalanchoe* had stronger roots than plants of the cultivar Nadia.
4. Flowers of plants of the new *Kalanchoe* were darker orange in color than flowers of plants of the cultivar Nadia.

BRIEF DESCRIPTION OF THE PHOTOGRAPH

The accompanying colored photograph illustrates the overall appearance of the new *Kalanchoe,* showing the colors as true as it is reasonably possible to obtain in colored reproductions of this type. Colors in the photograph may differ slightly from the color values cited in the detailed botanical description which accurately describe the colors of the new *Kalanchoe.* The photograph comprises a side perspective view of a typical potted plant of 'Zion'.

DETAILED BOTANICAL DESCRIPTION

In the following description, color references are made to The Royal Horticultural Society Colour Chart except where general terms of ordinary dictionary significance are used. Plants used for the aforementioned photograph and for the description were grown during the autumn in De Kawakel, The Netherlands, in a glass-covered greenhouse. During the production of the plants, day and night temperatures averaged 20° C. and light levels were about 500 Watt/$m^2$. Unrooted cuttings were directly stuck in 10.5-cm containers and received long day/short night conditions (about 15 hours of light) for about four weeks; plants then received photoinductive short day/long night conditions (minimum 15 hours darkness) until flowering. Plants were about 15 weeks old from an unrooted cutting when the photograph and the description were taken.

Botanical classification: *Kalanchoe blossfeldiana* cultivar Zion.

Parentage:

*Female or seed parent.*—Proprietary selection of *Kalanchoe blossfeldiana* identified as code number 93104-15, not patented.

*Male, or pollen, parent.*—Proprietary selection of *Kalanchoe blossfeldiana* identified as code number 95018, not patented.

Propagation:

*Type cutting.*—Terminal vegetative cuttings.

*Time to initiate roots.*—Summer: About 10 days at 20° C. Winter: About 14 days at 20° C.

*Time to produce a rooted young plant.*—Summer: About 21 days at 20° C. Winter: About 25 days at 20° C.

*Root description.*—Fine, fibrous; brown in color.

*Rooting habit.*—Freely branching; moderately dense.

Plant description:

*Form/growth habit.*—Upright and uniform plant habit. Very freely flowering with numerous compound cymes. Inverted triangle with rounded crown. Vigorous growth habit; rapid growth rate.

*Plant height at flowering.*—About 24 cm.

*Plant diameter at flowering.*—About 18 cm.

*Branching habit.*—Freely branching; typically seven lateral branches develop per plant. Pinching (removal of terminal apex) is not required but will enhance lateral branch development.

*Lateral branch description.*—Length: About 18 cm. Diameter: About 4 cm. Internode length: About 5 mm. Aspect: Erect. Strength: Strong. Texture: Smooth, glabrous. Color: Close to 147A.

*Foliage description.*—Arrangement: Opposite, simple; sessile. Length: About 10 cm. Width: About 6 cm. Shape: Elliptic. Apex: Obtuse. Base: Cuneate. Margin: Crenate; undulate. Texture, upper and lower surfaces: Leathery, glabrous and succulent. Color: Developing and fully expanded leaves, upper surface: Close to 147A. Developing and fully expanded leaves, lower surface: Close to 147B. Venation, upper and lower surfaces: Similar to lamina.

Flower description:

*Flower type and habit.*—Single flowers arranged in compound dichasial cymes that arise from leaf axils. Freely flowering; about 40 open flowers per lateral branch and about 200 open flowers per plant. Flowers persistent. Flowers not fragrant.

*Natural flowering season.*—Plants of the new *Kalanchoe* initiate and develop flowers under short day/long night conditions or during the late autumn/winter/early spring. Flower initiation and development can also be induced under artificial short day/long night conditions (at least 14 hours of darkness).

*Time to flower.*—Under short day/long night photoinductive conditions, about ten weeks are required. Actual time to flower is primarily dependent upon temperature and light intensity.

*Post-production longevity.*—Excellent post-production longevity; plants maintain good foliage and flower substance for about five weeks under interior environmental conditions.

*Inflorescence height.*—About 13 cm.

*Inflorescence diameter.*—About 20 cm.

*Flower diameter.*—About 9 mm.

*Flower height.*—About 1.3 cm.

*Flower buds.*—Shape: Elongated ovoid. Length: About 1 cm. Width: About 2 mm. Color: 138D.

*Petals.*—Quantity: Four fused at base. Length: About 7 mm. Width: About 5 mm. Shape: Ovate. Apex: Cuspidate. Margin: Entire. Texture, upper and lower surfaces: Glabrous, smooth. Color: When opening, upper surface: 34A. When opening, lower surface: 36A. Fully opened, upper surface: 40C; color becoming closer to 40D with development. Fully opened, lower surface: 29D and 38D.

*Sepals.*—Quantity: Four fused at base. Length: About 5 mm. Width: About 1.5 mm. Shape: Lanceolate. Apex: Acute. Base: Obtuse. Margin: Entire. Texture, upper and lower surfaces: Glabrous, smooth. Color, upper and lower surfaces: 144A.

*Peduncles.*—Length: About 3 to 4 mm. Diameter: About 1 mm. Aspect: Erect. Strength: Strong. Texture: Smooth, leathery. Color: Close to 138C.

*Reproductive organs.*—Stamens: Quantity per flower: Eight. Anther shape: Oval. Anther length: About 1 mm. Anther color: Yellow. Pollen amount: Moderate. Pollen color: Yellow. Pistils: Quantity per flower: Four. Style length: About 4 mm. Style color: Light green. Stigma shape: Rounded. Stigma color: Light green. Ovary color: Green.

*Seed.*—Length: About 0.05 mm. Diameter: About 0.025 mm. Color: Brownish black.

Disease/pest resistance: Plants of the new *Kalanchoe* have not been observed to be resistant to pathogens and pests common to *Kalanchoes.*

Temperature tolerance: Plants of the new *Kalanchoe* have been observed to tolerate low temperatures of 17° C. and high temperatures of 40° C.

It is claimed:

1. A new and distinct cultivar of *Kalanchoe* plant named 'Zion', as illustrated and described.

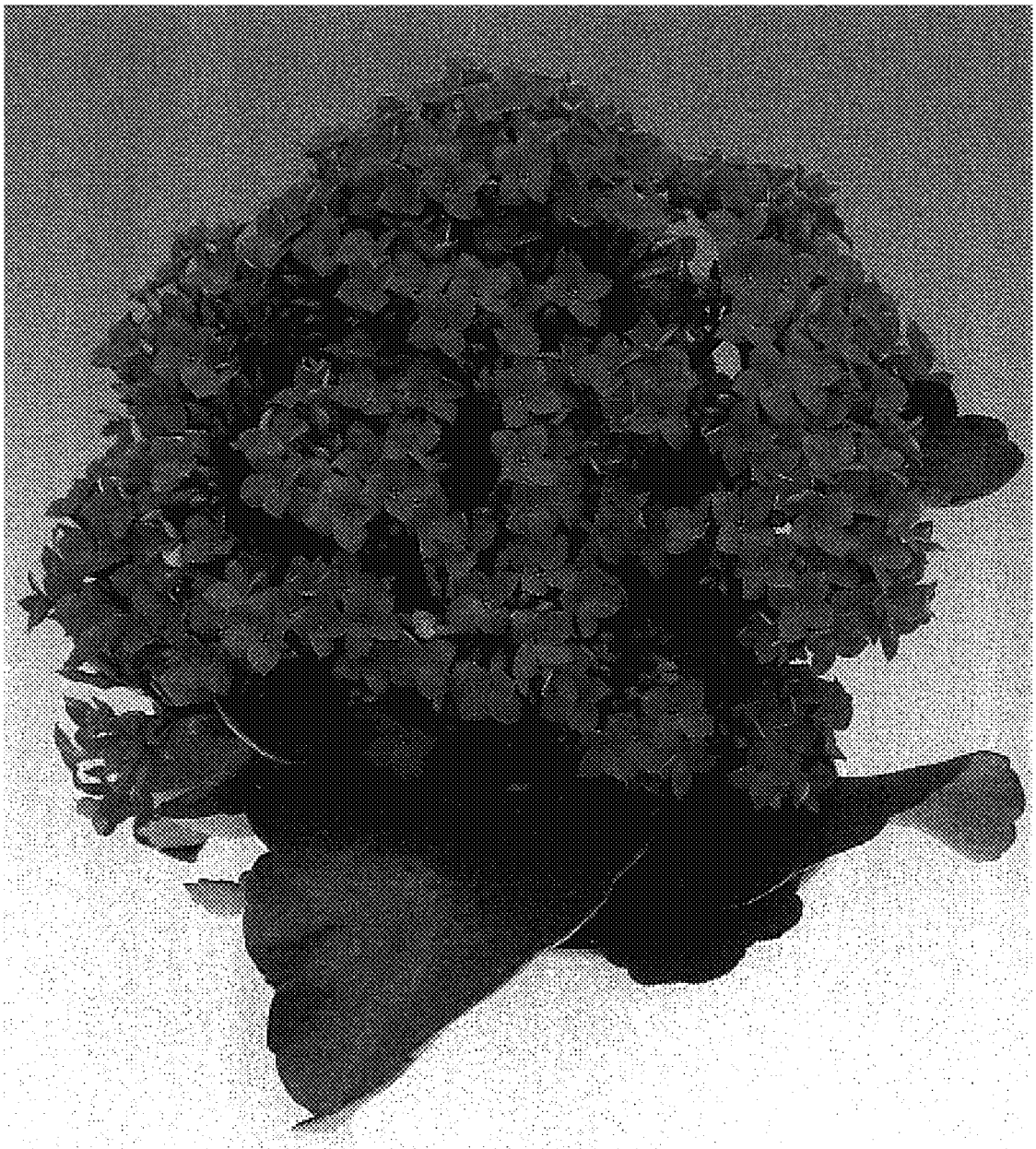

* * * * *